United States Patent [19]
Walker et al.

[11] Patent Number: 5,364,354
[45] Date of Patent: Nov. 15, 1994

[54] EXCHANGEABLE INTEGRATED-WIRE BALLOON CATHETER

[75] Inventors: Blair D. Walker, Long Beach; Sheryl W. Higgins, Silverado, both of Calif.

[73] Assignee: Baxter International Inc., Deerfield, Ill.

[21] Appl. No.: 970,581

[22] Filed: Oct. 22, 1992

Related U.S. Application Data

[63] Continuation of Ser. No. 690,447, Apr. 24, 1991, abandoned.

[51] Int. Cl.⁵ ............................................. A61M 29/00
[52] U.S. Cl. ...................................... 604/96; 606/194
[58] Field of Search .................. 604/96, 99, 100, 101, 604/167; 606/192–194

[56] References Cited

U.S. PATENT DOCUMENTS

| | | |
|---|---|---|
| 4,994,018 | 2/1991 | Saper . |
| 5,045,061 | 9/1991 | Seifert et al. . |
| 5,102,390 | 4/1992 | Crittenden et al. . |
| 5,135,487 | 8/1992 | Morrill et al. . |
| 5,135,494 | 8/1992 | Engelson et al. . |
| 5,171,221 | 12/1992 | Samson . |
| 5,192,295 | 3/1993 | Danforth et al. . |

FOREIGN PATENT DOCUMENTS

3935579 10/1989 Germany .
WO92/08510 5/1992 WIPO .

*Primary Examiner*—John D. Yasko
*Attorney, Agent, or Firm*—Debra D. Condino; Raymond Sun

[57] ABSTRACT

A fully exchangeable integrated-wire dilation catheter for performing angioplasty is disclosed having a flexible small diameter guide wire provided with an enlarged diameter distal end portion and a flexible elongated tubular shaft with at least one dual function fluid conducting lumen adapted to receive the guide wire extending therethrough. The distal end of the tubular shaft is connected to the proximal end of an expandable balloon provided with a coaxially aligned distal orifice having means for releasably engaging the enlarged distal end portion of the guide wire in sealing relationship. In a preferred embodiment the sealing means is a flexible sleeve extending from the distal orifice of the expandable balloon and dimensioned to slidingly engage the correspondingly sized enlarged distal end portion of the guide wire. Associated procedures for utilizing the dilation catheter are also disclosed.

21 Claims, 4 Drawing Sheets

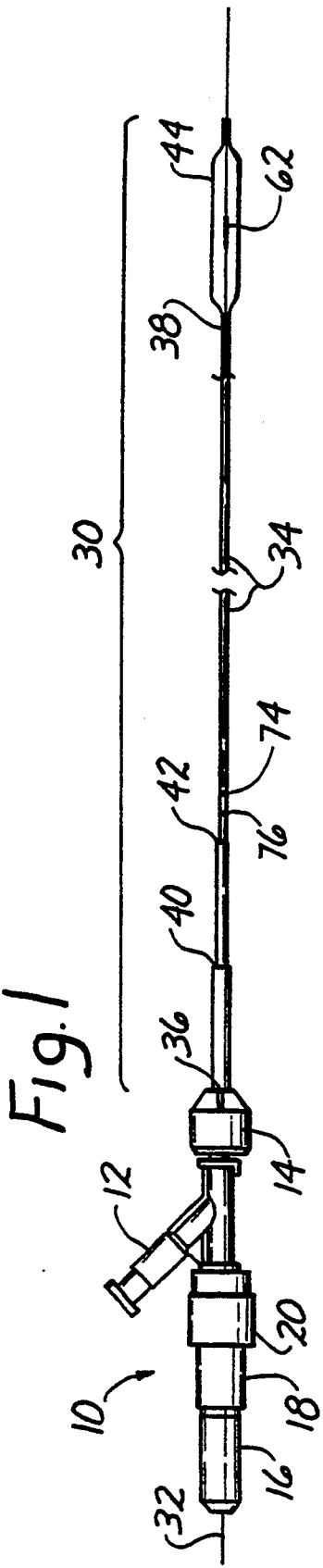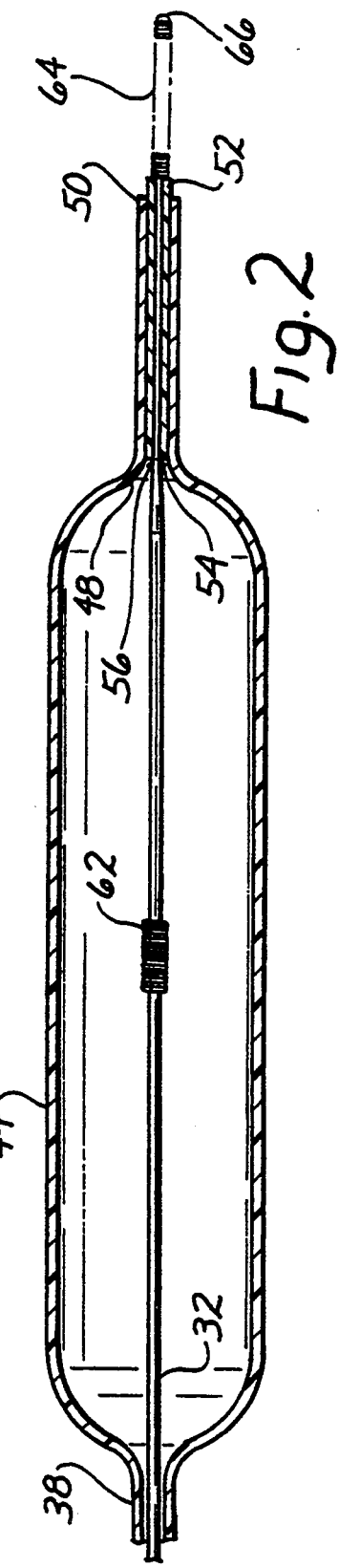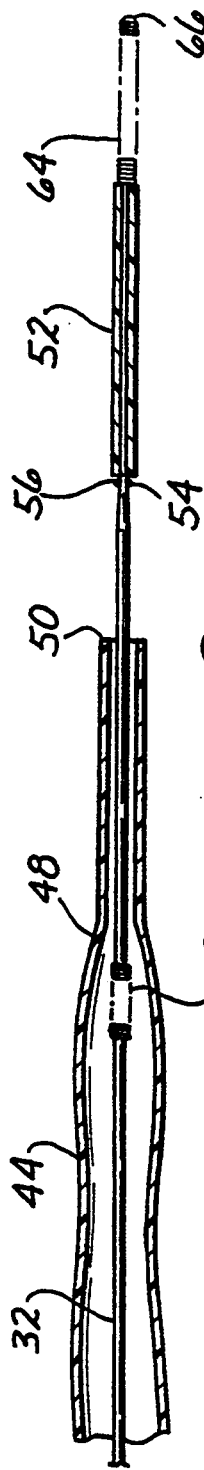

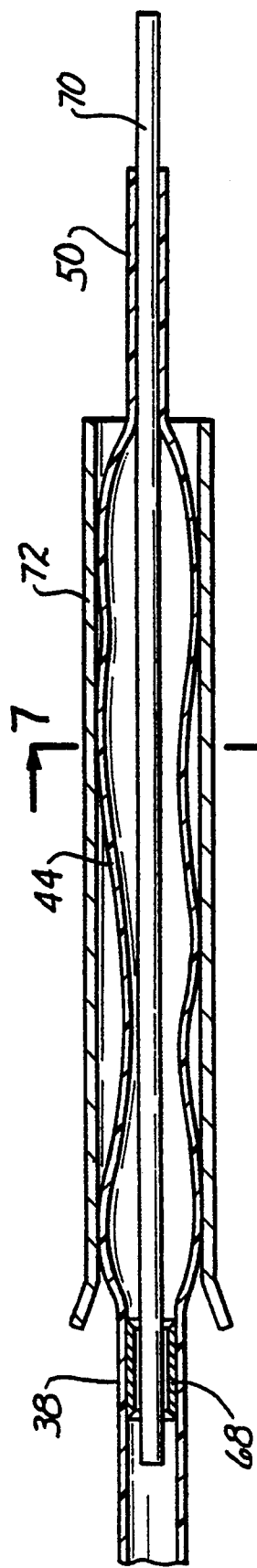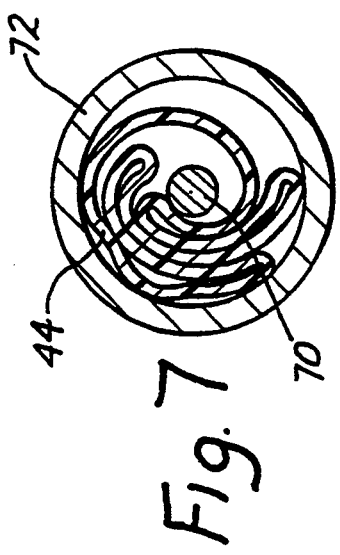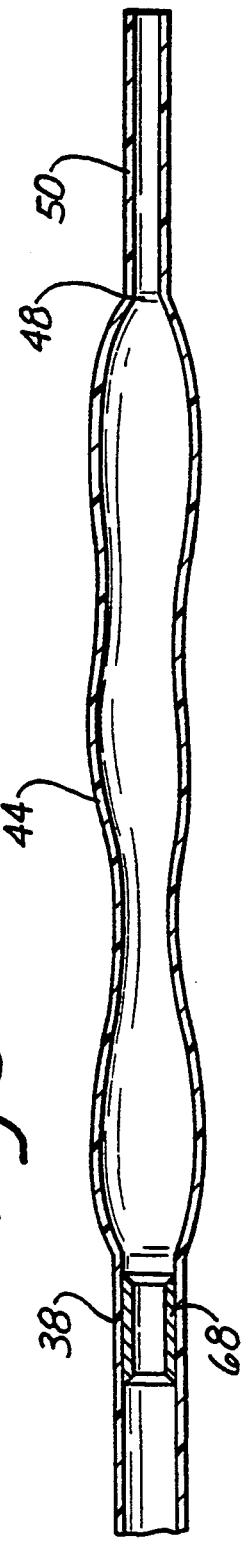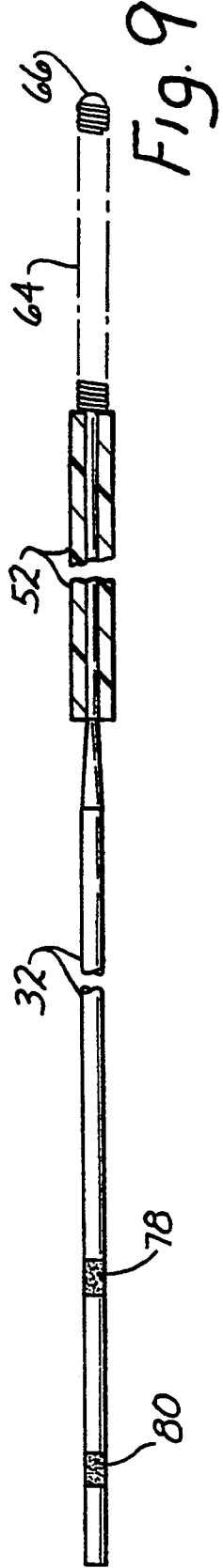

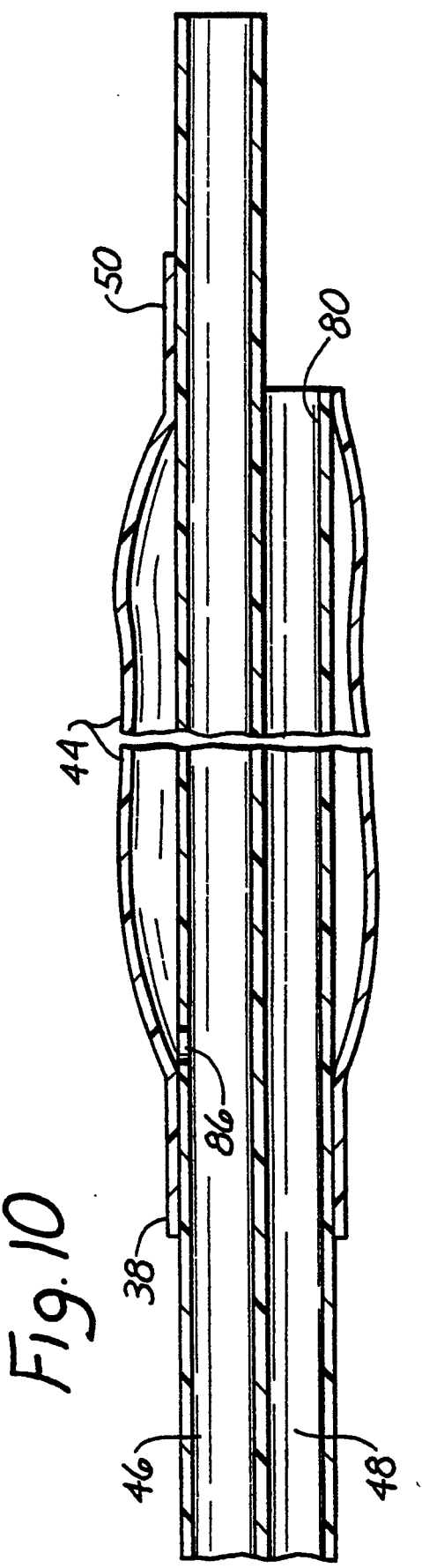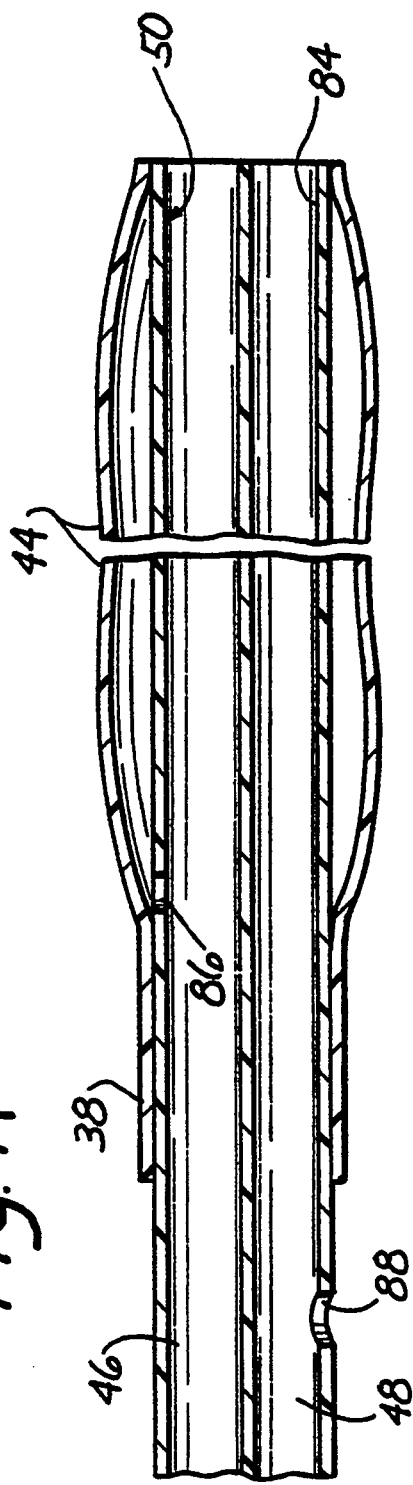

EXCHANGEABLE INTEGRATED-WIRE BALLOON CATHETER

This application is a continuation of Ser. No. 07/690,447 filed Apr. 24, 1991 now abandoned.

FIELD OF THE INVENTION

The present invention relates in general to the field of dilation or balloon catheters employed in the treatment of vascular diseases. More particularly, the present invention relates to an integrated or fixed-wire balloon catheter assembly which can be positioned quickly and easily for use in opening vascular stenoses yet which provides the additional advantage of rapid balloon removal or replacement while retaining wire guided access to the stenotic lesion.

BACKGROUND OF THE INVENTION

Over the last decade the medical procedure known as angioplasty has become widely accepted as a safe and effective method for treating various types of vascular diseases. For example, angioplasty is widely used for opening stenoses throughout the vascular system and particularly for opening stenoses in coronary arteries. At present, the most common form of angioplasty is called percutaneous transluminal coronary angioplasty (PTCA). This procedure utilizes a dilation catheter having an inflatable balloon at its distal end. Using a fluoroscope and radiopaque dyes for visualization the distal end of the dilation catheter is guided into position through a guide catheter and across the stenosis and the balloon is inflated for a brief duration to open the artery and establish adequate blood flow. Typically, inflation of the balloon is accomplished by supplying pressurized fluid through an inflation lumen in the catheter which is connected to an inflation apparatus located outside the patient's body. Conversely, applying a negative pressure to the inflation lumen collapses the balloon to its minimum dimension for initial placement or removal of the balloon catheter within the target blood vessel.

In the past years a number of balloon catheter designs have been developed which have contributed to the safety and acceptability of PTCA and similar medical procedures. The most common design is known as an "over-the-wire" balloon catheter. This prior art device typically utilizes a relatively large lumen for passage of a guide wire and injection of angiographic visualization dye to assist in the placement of the device. A second parallel lumen is provided for inflation and deflation of the balloon. Typically, a steerable guide wire is positioned within the larger lumen and the entire assembly is maneuvered into an initial position within the target artery through a previously positioned large diameter guide catheter. Once near the site of the stenoses the guide wire can be rotated and axially extended or retracted into position across the lesion. The catheter is subsequently advanced along the guide wire to position its balloon end across the lesion prior to inflation of the balloon and dilation of the stenosis.

Though successful at opening stenotic lesions, these dual lumen catheters are relatively bulky and stiff which makes their use difficult for any lesions except those that are proximal and localized in nontortuous, easily accessible vessels. Moreover, these early design over-the-wire balloon catheters require an additional implanting physician or assistant to control the guide wire during positioning of the assembly because catheter and wire movement are independent of one another. This complex coordinated activity requires both experience and skill and may result in a slower insertion procedure than desired.

An alternative over-the-wire catheter assembly utilizes a non-removable guide wire that allows for longitudinal or axial movement. However, this design has a significant drawback because the entire non-removable guide wire catheter assembly must be removed to accomplish replacement or exchange of the balloon. In some cases of PTCA it is necessary to replace the balloon with one of different diameter or configuration following the initial dilation. Additionally, cases of acute reclosure have been noted where the lesion recloses following dilation and removal of the balloon catheter. This alternative system increases the difficulties of these subsequent procedures by requiring that the replacement catheter renegotiate the entire placement path without the advantage of a guide wire.

A "monorail" variant of the standard balloon-over-a-wire system also has been developed where only the distal portion of the balloon catheter tracks over the guide wire. This system utilizes a conventional inflation lumen and a relatively short guiding or through lumen at the distal end. Its principal benefits are the reduction of frictional drag over the length of the externally located guide wire and the ease of balloon exchange. It provides the ability to recross an acutely closed vessel or to exchange balloons without removing the guide wire. However, a disadvantage of this design is the increased difficulty in steering the guide wire because the guide wire is not supported by the balloon catheter. Additionally, the dual lumen distal design produces a larger profile and shaft size.

Another prior art innovation in dilation catheter design is the "fixed-wire" or integrated "balloon-on-a-wire" dilation catheter. These single lumen designs utilize a relatively narrow wire positioned within the inflation lumen and permanently fixed to the distal end of the balloon. This produces a low-profile assembly which is able to cross severely narrowed lesions and to navigate tortuous vascular pathways. Additionally, the fixed guide wire bonded at the distal end of the balloon improves the steerability and pushability of these designs which enhances their maneuverability. The thin shaft design also improves coronary visualization and enables all but the tightest critical lesions to be crossed. However, though able to provide relatively quick and simple balloon placement as well as providing access to lesions otherwise unsuitable for PTCA, balloon-on-a-wire systems sacrifice the ability to maintain guide wire position across the lesion when exchanging balloons or the safety advantage of being able to recross an acutely closed vessel without repositioning the entire assembly.

Accordingly, it is an object of the present invention to provide a balloon-on-a-wire dilation catheter which incorporates all of the benefits of a small diameter fixed wire system yet allows for removal, reengagement or replacement of the balloon while leaving the guide wire in place to preserve an easily renegotiated path along the blood vessel being treated.

It is an additional object of the present invention to provide an integrated-wire dilation catheter offering an extremely low profile and a small shaft size to facilitate maneuverability and placement of the catheter as well as to provide it with the ability to negotiate tortuous vessels and to pass highly stenosed lesions.

It is a further object of the present invention to provide an integrated-wire balloon catheter having a steerable guide wire releasably fixed inside the catheter to provide enhanced torqueability, pushability, and maneuverability in order to facilitate the rapid, single operator placement and positioning of the assembly.

SUMMARY OF THE INVENTION

These and other objects are achieved by the exchangeable integrated-wire balloon catheter of the present invention which, in accordance with broad structural aspects thereof, includes at least a single-lumen balloon catheter having a seal at its distal end which releasably engages the enlarged distal end portion of a flexible guide wire running the length of the catheter. This unique construction allows rotational and longitudinal movement of the guide wire relative to the balloon catheter where desired and, if necessary, allows the catheter to be removed and reengaged or fully exchanged over the guide wire. Further, additional lumens may be incorporated into the basic catheter design to carry drugs, blood, fluids and the like or to allow blood to passively perfuse the distal artery during balloon inflation.

More specifically, the flexible guide wire of the present invention is formed of metal, polymeric material or a combination of both and is provided with a relative small cross-sectional diameter to increase its flexibility and to reduce the overall cross-sectional profile of the dilation catheter assembly. However, unlike prior art guide wire designs the distal end portion of the guide wire steps up to a larger outer diameter. The catheter assembly of the present invention positions the small diameter proximal portion of the guide wire along the length of the axial lumen of the elongated tubular shaft of the balloon catheter and through the balloon itself. The expandable balloon portion of the catheter is connected to the distal end of the tubular shaft in a sealing or fluid conducting arrangement with the axial lumen. The distal end of the expandable balloon is provided with an orifice that is coaxially aligned with the axial lumen and adapted to receive or conduct the guide wire. The distal orifice in turn is provided with means for releasably engaging the enlarged diameter distal end portion of the guide wire in a sealing relationship to allow for pressurization and inflation of the balloon and to fix the wire within the catheter in order to facilitate maneuvering the assembly during placement.

In this manner, the present invention combines the functions of fluid conducting and guide wire transmittal in a single lumen as opposed to the prior art dual-lumen balloon catheter designs. This unique construction provides an exchangeable balloon catheter having an exceptionally small insertion profile and all of the advantages previously associated with non-exchangeable fixed-wire catheters; yet it also provides the advantage of the ability to leave its guide wire in position across a vascular lesion during balloon exchange or removal.

In a preferred embodiment of the present invention the means for releasably engaging the enlarged diameter distal end portion of the guide wire in sealing relationship is a resilient sleeve which extends from the distal orifice of the expandable balloon. This sleeve is dimensioned to slide over the enlarged diameter distal end portion of the guide wire as the catheter is advanced distally along the wire. Preferably, the distal portion of the wire is formed to have a smoothly surfaced, cylindrical cross section as this construction allows the resilient sleeve to seal against the distal end portion of the guide wire. Additionally, it provides sufficient freedom of movement to allow the guide wire to rotate in place in order to facilitate the manipulation of the balloon catheter into position within a vascular pathway.

Sliding the catheter proximally relative to the internal guide wire (or vis versa) slips the resilient sleeve off of the enlarged diameter distal end portion of the guide wire onto the smaller diameter proximal portion of the wire. The unseating of the resilient sleeve from the enlarged diameter distal end portion of the guide wire breaks the seal at the distal catheter end. In this position the guide wire can be advanced axially along the longitudinal axis of the catheter to cross narrow or irregular lesions or to follow a tortuous vascular pathway. Similarly, following dilation the guide wire can be left in place across the stenotic lesion as the disengaged balloon is partially withdrawn along the wire to verify dilation and blood flow. If necessary, the balloon can be readvanced distally along the wire until the resilient sleeve sealingly reengages the distal end portion of the guide wire. Following reengagement the balloon can be reinflated. As those skilled in the art will appreciate, a complete exchange of the balloon is possible without retracking the pathway utilizing the same general procedure along the positioned guide wire.

To facilitate visualization of the guide wire and balloon catheter during angioplasty the apparatus of the present invention is preferably provided with one or more radiopaque markers. Typically, these markers are formed of small coils, strips or spheres of gold, platinum or other dense, relatively inert metal. In one embodiment of the present invention a radiopaque spring coil of flexible wire is provided distally to the enlarged diameter distal end portion of the guide wire. Similarly, in alternative embodiments of the present invention radiopaque markers are located along the guide wire at positions proximal to the enlarged distal end portion of the wire. It is also contemplated as being within the scope of the present invention to position radiopaque markers on the balloon catheter to enable the coronary physician to visualize the placement of the balloon relative to the guide wire and stenotic lesion.

Other features and advantages of the present invention will become apparent from the following detailed description, taken in conjunction with the accompanying drawings which illustrate, by way of example, the principals of the present invention.

BRIEF DESCRIPTION OF THE DRAWINGS

FIG. 1 is a partial fragmentary view in elevation of an integrated-wire dilation catheter illustrating the principals of the present invention.

FIG. 2 is an enlarged cross-sectional view of the distal portion of the balloon catheter of FIG. 1.

FIG. 3 is a partial sectional view of the distal portion of the balloon catheter of FIG. 2 shown in a collapsed modified position.

FIG. 6 is an enlarged cross-sectional view of the distal end portion of a replacement balloon catheter illustrating additional features of the present invention.

FIG. 7 is a cross section of the balloon catheter of FIG. 6 taken along the line VII—VII.

FIG. 8 is an enlarged sectional view of the replacement balloon catheter of FIG. 6 minus its packaging mandrel and cover.

FIG. 9 is a partial fragmentary view of an alternative guide wire illustrating additional features of the present invention.

FIG. 10 is an enlarged cross-sectional view of the distal portion of an alternative dual-lumen balloon catheter illustrating additional features of the present invention.

FIG. 11 is an enlarged cross-sectional view of the distal portion of an alternative dual-lumen balloon catheter illustrating additional features of the present invention.

DETAILED DESCRIPTION

Figure 4:
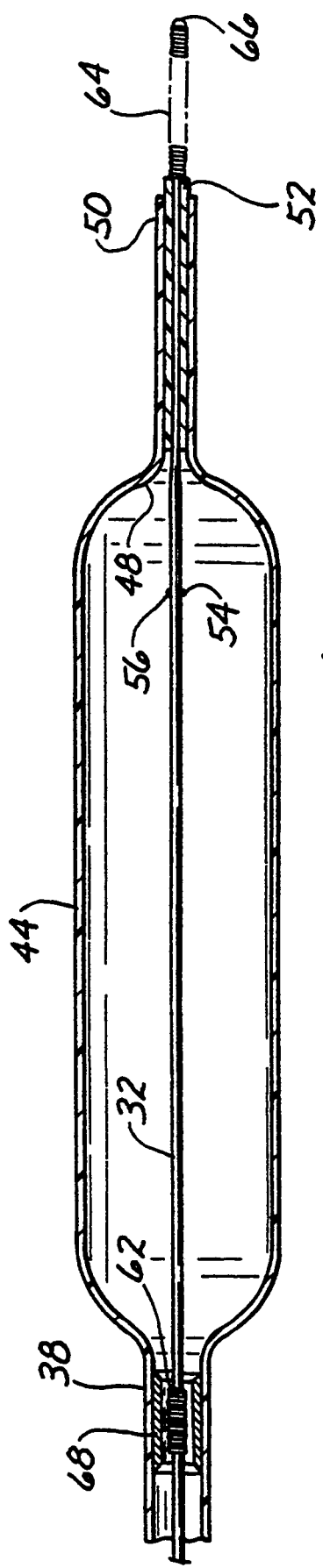
FIG. 4 is a sectional view of the distal portion of an alternative embodiment of the present invention illustrating additional features thereof.

Referring more particularly to the drawings in which similar elements are indicated by identical reference numerals, FIG. 1 shows a Y-connector generally indicated by reference 10 which is provided with an inflation port 12 and a compression hub 14 for sealing a catheter body to Y-connector 10. Drum 16 located at the proximal end of connector 10 is capable of axial rotation and is provided with a pin-vise 18 for securely holding a catheter guide wire in position. Hemostatic seal 20 is provided to prevent fluid leakage. Preferably, seal 20 is adjustable or releasable as this facilitates the removal or exchange of the catheter. Though not essential to the practice of the present invention, drum 16 of Y-connector 10 provides a catheter implant physician with the ability to rotate the catheter guide wire clamped in pin-vise 18 in order to steer the advancing catheter through the desired vascular pathway without assistance. Additionally, as will be discussed in detail below, Y-connector 10 effectively seals the proximal end of the catheter to maintain working pressure while allowing rotational inputs to be directed to the guide wire.

An exemplary embodiment of the fully exchangeable, integrated-wire, dilation balloon catheter of the present invention is shown generally as reference 30 in FIG. 1 secured to compression hub 14 of Y-connector 10 and comprising a flexible, small diameter guide wire 32 extending through Y-connector 10 and along a flexible, elongated tubular shaft 34 having a proximal end 36 and a distal end 38. Flexible tubular shaft 34 is preferably formed of a polymeric material such as polyethylene, polyamide, polyimide, polypropylene, polyvinyl, polyester such as polyethyleneterephthalate (PET), or polyolefin copolymer. Additionally, shaft 34 may be coated with PTFE, silicone or other materials including low friction lubricants. As shown in FIG. 1, proximal end 36 of shaft 34 may be provided with additional protective sleeves 40 and 42 to strengthen the junction of shaft 34 to Y-connector 10 and prevent kinking of the shaft during manipulation and placement of catheter 30.

Distal end 38 of shaft 34 flares into an expandable dilation balloon 44 (shown inflated), the details of which are more readily apparent in the enlarged cross section of FIG. 2. As shown in FIG. 2, dilation balloon 44 is formed as an integral part of catheter 30 in fluid conducting communication with an exemplary single, axial lumen 46 running throughout the length of tubular shaft 34. Though the integral construction of catheter 30 illustrated may be preferred, alternative constructions may be utilized so long as dilation balloon 44 is sealingly connected to distal end 38 of tubular shaft 34. Accordingly, dilation balloon 44 may be constructed of the same or different polymeric materials utilized in the construction of shaft 34. Similarly, low friction coatings such as PVC, polyamide or fluoropolymer or such as PTFE or hydrophilic materials and lubricants may be utilized to enhance the movement of all components of catheter 30 during angioplasty.

Balloon 44 is provided with a distal orifice 48 which is coaxially aligned with lumen 46 and adapted to receive and conduct guide wire 32 which extends throughout the length of balloon 44 and beyond distal orifice 48. Orifice 48 is provided with means for releasably engaging guide wire 32 in a sealing relationship. In the exemplary embodiment of the present invention the means for releasably engaging in sealing relationship is formed of a resilient sleeve 50 which extends from distal orifice 48 and is dimensioned to slidingly engage an enlarged diameter distal end portion of guide wire 32 formed from a cylindrical collar 52 which is sealingly coupled to guide wire 32. Resilient sleeve 50 may be formed from the same material forming the remainder of tubular shaft 34 or may be formed from a lubricuous polymeric material. Alternatively, resilient sleeve 50 may be coated along its inner surface with a lubricuous material to facilitate its engagement with cylindrical collar 52. Cylindrical collar 52 can be formed of a wide variety of materials ranging from stainless steel to polymeric materials and may even be formed as an integral part of wire 32. However, it is preferred that collar 52 be formed of a polymeric material such as PVC, polyamide, polyimide, or fluoropolymer such as polytetrafluoroethylene (PTFE) as this provides an added degree of flexibility to the enlarged cross-sectional diameter distal end portion of wire 32 formed by collar 52. An additional advantage of forming collar 52 from materials such as PTFE is that cylindrical collar 52 may be sealingly coupled to guide wire 32 yet retain the ability to slide axially along guide wire 32. As shown in FIG. 2, to retain polymeric cylindrical collar 52 in position along guide wire 32 one or more retaining beads 54 and 56 may be soldered or brazed to guide wire 32. Alternatively, adhesives or a simple mechanical fit may be utilized. It should also be noted that guide wire 32 and specifically cylindrical collar 52, may be formed from a lubricious polymeric material or provided with a thin coating of silicone, fluoropolymer or the like to increase its lubricity.

This exemplary construction produces a releasably engaging seal which fixes guide wire 32 in position relative to balloon 44 yet allows guide wire 32 to be rotated freely without wrapping balloon 44 about the shaft of guide wire 32. Additionally, as shown in the alternative embodiment of the present invention illustrated in FIG. 4, where retaining beads 54 and 56 are soldered somewhat proximally to the distal location of cylindrical collar 52, collar 52 is provided with an added degree of sliding axial movement along guide wire 32 which allows the positioning physician to extend or retract the end portion of guide wire 32 relative to balloon 44 where necessary while retaining the seal between collar 52 and sleeve 50.

It should be noted that retaining beads 54 and 56 create an outer diameter which is larger than the inner diameter of cylindrical collar 52 yet smaller than the outer diameter of cylindrical collar 52. As shown in FIG. 3, this construction enables the sealing means of resilient sleeve 50 to be slidingly advanced or retracted along the cylindrical length of collar 52 in order to releasably engage the sealing means of the present invention. In FIG. 3 balloon 44 has been deflated and retracted proximally along guide wire 32 to a position where resilient sleeve 50 has completely disengaged from cylindrical collar 52. It is important to note that as shown in FIGS. 2 and 3 all portions of guide wire 32 proximal to its enlarged diameter distal end portion formed by cylindrical collar 52 have a cross-sectional diameter smaller than that of the outer diameter of collar 52. This construction allows the balloon catheter of the present invention to be completely advanced or retracted along the entire longitudinal extent of guide wire 32 for the purposes of balloon manipulation, removal or replacement.

Thus, the balloon catheter can be replaced with a catheter having a balloon provided with a different expandable diameter if necessary to reopen a particularly difficult stenotic lesion. Similarly, if problems develop with the inflation of balloon 44 during angioplasty it is possible to replace the balloon with a properly functioning device. All the vascular physician need do is to retract tubular shaft 34 and balloon 44 along guide wire 32 leaving guide wire 32 in position across the target lesion. Then, a replacement balloon can be advanced along the positioned guide wire without having to retrace the entire vascular pathway. As those skilled in art will appreciate, this greatly facilitates the speed and safety of such a procedure. In order to reengage the balloon on collar 52 the vascular physician simply advances the catheter along guide wire 32 to slide resilient sleeve 50 over cylindrical collar 52. Generally, in practice, when advancement of resilient sleeve 50 relative to collar 52 ceases a sealing engagement has been accomplished. The complete engagement shown in FIG. 2 is for purposes of illustration only. Further details of the balloon exchange or replacement procedure in accordance with the teachings present invention will be discussed with respect to FIGS. 6–8.

To facilitate the functioning of the releasably sealing means of the present invention it is preferred that collar 52 have a generally uniform circular cross section to define a smooth cylindrical outer surface. However, as shown in FIG. 5, it is contemplated as being within the scope of the present invention to provide collar 52 with a slightly tapering proximal end to ease the initial engagement of resilient sleeve 50 over collar 52 as balloon 44 is advanced along guide wire 32. Additionally, to provide a more secured sealing engagement collar 52 can be configured to include circumferential groove 60. Alternatively, the proximal end of collar 52 adjacent to retaining beads 54 and 56 may be provided with a hemispherical cross section for the same purposes as is shown in the alternative embodiment of FIG. 4. Similarly, beads 54 and 56 can be configured for this purpose.

It also should be emphasized that axial lumen 46 of the present invention is configured to perform a dual role. As shown in FIG. 2, a diameter of axial lumen 46 is greater than that of guide wire 32. By virtue of this construction, axial lumen 46 is adapted to both receive guide wire 32 and to conduct an inflation fluid to and from balloon 44. This dual function design produces an ultra-low profile device which significantly enhances its ability to cross very tight stenoses or to traverse particularly difficult vascular pathways. As an additional benefit, larger volumes of radiographic visualization dyes may be injected about tubular shaft 34 to enhance its visibility during placement of the apparatus relative to the larger diameter balloon catheters of the prior art.

Along these lines, exemplary non-limiting dimensions for the balloon catheter assembly of the present invention may be as follows. For example, as is typical in the coronary arts, the overall length of catheter 30 will typically range from 120 cm to 160 cm. The axial length of dilation balloon 44 will comprise approximately 1 cm to 4 cm of this overall length. Typically, dilation balloons are available in stepped dilation diameters ranging from approximately 1.0 mm to 5.0 mm in 0.5 mm or 0.25 mm increments. As known in the art, these inflation diameters are typically characterized at 6 to 10 atmospheres of pressure. Naturally, the deflated profile of the dilation balloons increases slightly with the final dilation diameter. However, while the majority of prior art balloon catheters have a deflated balloon profile measuring approximately 0.04 inches in diameter, the balloon catheter of the present invention has a typical dilated balloon profile of only 0.03 inches. Similarly, the dual function, single lumen design of the present invention produces a tubular shaft having a correspondingly narrow profile.

Exemplary non-limiting diameters for the proximal portion of guide wire 32 range from 0.005 to 0.016 inches whereas the preferred exemplary outer diameter of cylindrical collar 52 ranges from approximately 0.012 to 0.018 inches. Thus, in the embodiments of the present invention illustrated in FIGS. 2–5 the distal end portion of guide wire 32 is provided with a cross-sectional diameter on the order of approximately 0.005 inches and cylindrical collar 52 is formed of a polymeric material such as PTFE having an outer diameter of approximately 0.016 inches and a wall thickness of approximately 0.005 inches. It should be emphasized that the proximal diameter of guide wire 32 need not be constant and may taper to provide an enhanced degree of flexibility toward the distal end of guide wire 32. Guide wire 32 itself is preferably formed of metal such as stainless steel but also may be constructed of polymers or polymer coated metals as is known in the art. An exemplary overall wire length for guide wire 32 is on the order of 175 cm. The cross section of guide wire 32 proximal to cylindrical collar 52 need not be circular to be within the scope of the present invention. For example, generally elliptical or ribbon-like configurations may be utilized to provide an enhanced degree of flexibility.

Also visible in FIG. 2 is radiopaque marker 62 formed of a coil of dense metal such as gold or platinum fixed at a position adjacent to the distal end portion of wire 32. Marker 62 can be secured to guide wire 32 in any manner known in the art including soldering, brazing, adhesives, or simple mechanical deformation. Radiopaque marker 62 functions to provide the implanting physician with a readily apparent visual reference which be viewed on a fluoroscope during the angioplasty procedure. During positioning of the apparatus the surgeon simply manipulates the catheter guide wire assembly of the present invention until marker 62 is positioned directly adjacent or across the target lesion. Because of its positioning on guide wire 32 relative to dilation balloon 44, when marker 62 is so positioned dilation balloon 44 is positioned across the lesion as well.

Though not essential to the practice of the present invention, guide wire 32 is preferably provided with a flexible spring coil 64 positioned distally to enlarged diameter cylindrical collar 52. As shown in FIGS. 2–5, spring coil 64 is preferably provided with a smooth hemispherical tip 66 in order to reduce vascular trauma as guide wire 32 is advanced along a vascular pathway. Spring coil 64 may be formed of any resilient material, preferably metal, and in the preferred embodiment of the present invention is formed of a radiopaque material such as platinum or gold. Thus, spring coil 64 functions as an additional marker to assist the coronary physician in positioning the apparatus of the present invention. For example, when spring coil 64 has been advanced to a position just beyond the target lesion the physician may be comfortable in knowing that balloon 44 is properly positioned across the lesion. At that point, as long as resilient sleeve 50 is sealingly engaging cylindrical collar 52 balloon 44 may be inflated by pumping a pressurized fluid such as saline or contrast medium along axial lumen 46. Following dilation, a negative pressure can be applied to axial lumen 46 to deflate balloon 44 prior to its removal or disengagement from collar 52.

Figure 5:
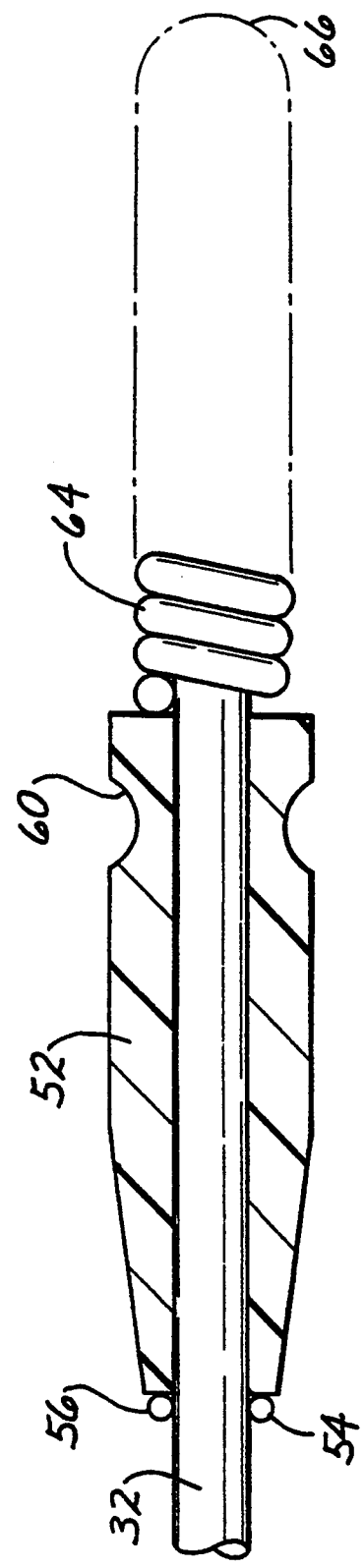
FIG. 5 is an enlarged partial sectional view of an alternative embodiment of the distal portion of the guide wire of the present invention.

In the alternative embodiment of the present invention shown in FIG. 4 the radiopaque markers formed by markers 62 and spring coil 64 are arranged in what is known as a "book end" position. In this configuration the implanting physician positions guide wire 32 such that spring coil 64 is distal to the target lesion and radiopaque marker 62 is proximal to the target lesion. In this manner, balloon 44 is positioned across the lesion. Additionally, in accordance with the teachings of the present invention catheter 30 itself can be provided with an additional radiopaque marker such as radiopaque ring 68 affixed to distal end 38 of tubular shaft 34. Radiopaque ring 68 enables the vascular physician to confirm that balloon 44 is properly positioned relative to collar 52 by lining up radiopaque ring 68 with radiopaque marker 62. This may be particularly helpful during reengagement of sleeve 50 with cylindrical collar 52.

Though spring coil 64 is illustrated in FIGS. 2–5 as being relatively straight, it is commonly known in the art to precurve spring coil 64 so that the implanting physician can rotate wire 32 and direct tip 66 of wire coil 64 into specific vascular junctions to direct the entire assembly along the proper pathway. Rotational manipulation of wire 32, or "torquing" as it is referred to in the art, is accomplished by rotating drum 16 of Y-connector 10 which firmly clamps wire 32 in pin-vise 18. The axially resilient construction of guide wire 32 transmits this torque along the entire longitudinal extent of wire 32 to coil 64. However, because cylindrical collar 52 is preferably sealingly coupled to guide wire 32 in a rotatable manner this torque is not transmitted to balloon 44 and prevents balloon 44 from wrapping in a spiral fashion around guide wire 32. Alternatively, where cylindrical collar 52 is not rotatably fixed to wire 32, it is preferred that the outer surface of cylindrical collar 52 be very smooth to allow a certain degree of slippage between it and resilient sleeve 50. In this manner, balloon wrapping also can be prevented.

As noted above, the exchangeable integrated-wire balloon catheter of the present invention enables a vascular physician to exchange one catheter for a second catheter along the pre-positioned guide wire without having to retrace the entire vascular pathway with the guide wire. As those skilled in the art will appreciate, replacement balloons produced in accordance with the teachings of the present invention need not include a guide wire. Thus, illustrated in FIG. 6, an exemplary replacement catheter can be provided with its balloon 44 prefolded over disposable mandrel 70 and packaged in disposable balloon cover 72. Preferably, mandrel 70 is constructed of metal or plastic and approximates the outer diameter of collar 52. Additionally, mandrel 70 may be coated with lubricating materials such as PTFE or silicone. The cross section of FIG. 7 illustrates an exemplary folded profile of balloon 44 for use in packaging within balloon cover 72.

Turning next to FIG. 8, to position the replacement catheter over a guide wire mandrel 70 and balloon cover 72 are removed. This allows the folded balloon 44 illustrated in FIG. 8 to freely pass over the smaller diameter proximal portion of guide wire 32 (not shown) as the implanting physician advances the replacement catheter along the guide wire. This folded balloon arrangement also supplies additional columnar strength to the replacement catheter which enables the implanting physician to easily engage resilient sleeve 50 over collar 52 to seal and inflate balloon 44 as previously illustrated in FIGS. 3 and 4.

An additional feature of the present invention is the provision of exit markers 74 and 76 near proximal end 36 of tubular shaft 34 as shown in FIG. 1. Generally speaking, exit markers 74 and 76 inform the implanting physician that catheter 30 is advancing to a position near its intended target where the tip of the balloon 44 is about to exit the tip of the implanting or guiding catheter (not shown). At this point the implanting physician can activate a fluoroscope to assist in the visualization and final placement of the balloon across the target lesion. Preferably, as illustrated in FIG. 1, two exit markers are utilized. The first, marker 74 will preferably be positioned approximately 90 cm from the distal end of balloon 44 and can be utilized to indicate tip exit from a guide catheter positioned for a brachial approach. Similarly, marker 76 is preferably positioned approximately 100 cm from the distal tip of the catheter to indicate exit from the guide catheter during a femoral approach. Both markers 74 and 76 may be applied to catheter 30 through printing, stenciling, embossing or the like.

Along these lines, as illustrated in FIG. 9, it is also contemplated as being within the scope of the present invention to provide the proximal end of guide wire 32 with its own set of visual markers, 78 and 80, to assist the implanting physician in determining that sleeve 50 is engaged with cylindrical collar 52. For example, it is contemplated that marker 80 would be positioned approximately 170 cm from tip 66 of wire 32 and would signal that the replacement catheter is about to exit the guiding catheter. It should be noted that this positioning is appropriate for both the femoral and brachial approaches. However, marker 78 is preferably positioned approximately 150 cm from tip 66 of wire 32 and functions to assure the implanting surgeon that resilient sleeve 50 is engaged with cylindrical collar 52. In practice, the implanting physician would visually align marks 78 and 80 with the outer visual reference formed by the proximal end of drum 16 on Y-connector 10 illustrated in FIG. 1.

Alternative exemplary embodiments of the exchangeable integrated-wire dilation balloon catheter of the present invention are illustrated in FIGS. 10 and 11. Each of these alternative embodiments is provided with an additional fluid conducting lumen. More particularly, the alternative embodiment of FIG. 10 illustrates a catheter embodiment configured for distal infusion of drugs, blood or other fluids. In addition to lumen 46, this alternative embodiment includes a second lumen 82 which serves to conduct fluids from the proximal end 36 of catheter 30 to its outlet port 80 adjacent resilient sleeve 50 on balloon 44. It should be noted that either or both lumens may be sized to sealingly engage the enlarged distal end portion of the guide wire. In this alternative embodiment, a side opening or communication port 86 is provided in lumen 46 to enable lumen 46 to communicate with balloon 44 for purposes of inflation and deflation.

The alternative double lumen embodiment of the present invention illustrated in FIG. 11 is structured to allow the passage of blood from the proximal end of the catheter to the distal end of the balloon while balloon 44 is inflated. Thus, in addition to dual-function axial lumen 46 catheter 30 also is provided with a second lumen 82 which, in turn, is provided with at least one distal outlet port 84 and at least one proximal side opening or inlet port 88. Inlet port 88 allows blood to passively perfuse the distal artery during inflation of balloon 44 by providing a passageway for blood to enter additional lumen 82 through port 88 and exit through distal port 84.

Thus, the apparatus of the present invention provides an exchangeable integrated-wire balloon catheter that can be positioned within a vascular pathway by a single vascular physician. Because the apparatus of the present invention provides the maneuverability of a fixed-wire dilation catheter coupled with the benefits of an ultralow catheter profile it can be quickly and easily maneuvered into position across lesions that are critically narrowed and irregularly shaped. Following expansion of the balloon and dilation of the lesion the catheter of the present invention can be disengaged from the distal end of its guide wire and retracted back from the lesion to allow the surgeon to visualize blood flow while retaining guide wire access across the lesion. If necessary, the surgeon can advance the balloon and reengage the distal end of the guide wire to reseal the balloon for purposes of reinflation. Alternatively, while leaving the guide wire in place the surgeon can completely remove and replace the balloon catheter with one having alternative dimensions which, in turn, can be sealingly engaged with the distal end of the guide wire for inflation purposes or a conventional over-the-wire catheter may be advanced along the wire. Lastly, in cases of acute reclosure the guide wire of the present invention can be utilized to direct a perfusion catheter into position.

In closing it is to be understood that the embodiments of the invention disclosed herein are illustrative of the principals of the invention and that other modifications may be employed which are within the scope thereof. Thus, by way of example, but not of limitation, the resilient sleeve may be configured to extend into the dilation balloon as opposed to the outward configuration of the releasable sealing means illustrated. Accordingly, the present invention is not limited to that precisely as shown and described in the specification.

What is claimed:

1. A dilation catheter and guide wire combination comprising:
   a flexible, small diameter guide wire having an enlarged diameter distal end portion;
   a flexible elongated tubular shaft having a proximal end and a distal end and one axially extending fluid conducting lumen adapted to receive said guide wire extending therethrough; and
   an expandable balloon connected to said distal end of said tubular shaft in fluid conducting communication with said lumen and having a distal orifice coaxially aligned with said lumen and adapted to receive said guide wire, said distal orifice provided with means for releasably engaging in sealing relationship said enlarged diameter distal end portion of said guide wire;
   wherein said means for releasably engaging in sealing relationship comprises a resilient sleeve extending from said distal orifice and dimensioned to slidingly engage said enlarged diameter distal end portion of said guide wire.

2. The dilation catheter of claim 1 wherein said enlarged diameter distal end portion of said guide wire comprises:
   a cylindrical collar sealingly coupled to said guide wire.

3. The dilation catheter of claim 2 wherein said cylindrical collar is formed of a polymeric material.

4. The dilation catheter of claim 2 wherein said cylindrical collar is formed of metal.

5. The dilation catheter of claim 1 further comprising at least one radiopaque marker disposed adjacent to said enlarged diameter distal end portion of said guide wire.

6. The dilation catheter of claim 5 wherein said radiopaque marker comprises a flexible metallic coil extending beyond said enlarged diameter distal end portion of said guide wire.

7. The dilation catheter of claim 1 further comprising at least one radiopaque marker fixed adjacent to the proximal end of said expandable balloon.

8. A dilation catheter for use in conjunction with a flexible, small diameter guide wire having an enlarged diameter distal end portion, said dilation catheter comprising:
   a flexible elongated tubular shaft having a proximal end and a distal end and at least one axially extending fluid conducting lumen adapted to receive said guide wire extending therethrough; and
   an expandable balloon located at said distal end of said tubular shaft in fluid conducting communication with said lumen and having a distal orifice coaxially aligned with said lumen and adapted to receive said guide wire, said distal orifice provided with means for releasably engaging in sealing relationship said enlarged diameter distal end portion of said guide wire;
   wherein said means for releasably engaging in sealing relationship comprises a resilient sleeve extending from said distal orifice and dimensioned to slidingly engage said enlarged diameter distal end portion of said guide wire.

9. The dilation catheter of claim 8 wherein said elongated tubular shaft and said expandable balloon are formed of resilient polymeric material.

10. The dilation catheter of claim 9 wherein said polymeric material is selected from the group comprising homopolypers and copolymers of:
    polyvinylchoride, polyethylene, polyolefin, fluoropolymer, polyamide, polyester, polyimide, and polypropylene.

11. The dilation catheter of claim 3 wherein said polymeric material is selected from the group comprising:
    polyvinylchoride, polyamide, polyimide and fluoropolymer.

12. A dilation catheter and guide wire combination comprising:

a flexible, small diameter guide wire having proximal and distal ends, with a portion of said distal end being of a larger diameter than said guide wire;

a flexible elongated tubular shaft having a proximal end and a distal end and at least one axially extending fluid conducting lumen adapted to receive said guide wire extending therethrough; and an expandable balloon connected to said distal end of said tubular shaft in fluid conducting communication with said lumen and having a distal orifice coaxially aligned with said lumen and adapted to receive said guide wire, said distal orifice provided with means for releasably engaging said enlarged diameter distal end portion of said guide wire in releasably sealing relationship;

wherein said means for releasably engaging said enlarged diameter distal end portion of said guide wire is a resilient sleeve extending from said distal orifice.

13. The dilation catheter and guide wire combination of claim 12 wherein said larger diameter guide wire distal end is a cylindrical collar coupled to said guide wire distal end.

14. The dilation catheter of claim 12 wherein said elongated tubular shaft and said expandable balloon are formed of resilient polymeric material.

15. The dilation catheter and guide wire combination of claim 12 wherein said resilient sleeve is formed from a lubricious polymeric material.

16. The dilation catheter and guide wire combination of claim 12 wherein one of said lumens includes side openings.

17. A guide wire for use with a dilation catheter comprising:

a distal end portion provided with a generally cylindrical configuration having an outer diameter greater than the diameter of all portions of said guide wire proximal thereto and dimensioned to be releasably received into and seal a resilient sleeve provided in a distal end of said dilation catheter.

18. The guide wire of claim 17 wherein said distal end portion is formed of a lubricious polymeric material.

19. A method for performing angioplasty while retaining wire guided access to a target lesion, said method comprising the steps of:

providing a dilation catheter and guide wire combination including a flexible, small diameter guide wire having at least a portion of its distal end being of a larger diameter than all portions proximal thereto, a dilation catheter having a flexible elongated tubular shaft having a proximal end and a distal end and at least one axially extending fluid conducting lumen adapted to receive said guide wire extending therethrough, and an expandable balloon located at said distal end of said tubular shaft in fluid conducting communication with said lumen and having a distal orifice coaxially aligned with said lumen, said distal orifice provided with means for releasably engaging said enlarged diameter distal end portion of said guide wire in releasably sealing relationship;

positioning said expandable balloon across said target lesion;

inflating said expandable balloon to open said target lesion;

deflating said expandable balloon;

disengaging said means for releasably engaging said enlarged diameter distal end portion of said guide wire; and retracting said dilation catheter along said guide wire.

20. The method of claim 19 further comprising the additional steps of:

readvancing said retracted dilation catheter along said guide wire;

reengaging said means for releasably engaging in sealing relationship said enlarged diameter distal end portion of said guide wire; and reinflating said balloon.

21. The method of claim 19 further comprising the additional steps of:

exchanging said retracted dilation catheter with a second dilation catheter having an expandable balloon;

advancing said second dilation catheter along said guide wire to position said expandable balloon across a target lesion;

inflating said expandable balloon to open said target lesion; and deflating said expandible balloon.

* * * * *